(12) United States Patent
Kawamoto et al.

(10) Patent No.: US 10,466,204 B2
(45) Date of Patent: Nov. 5, 2019

(54) WELDING STATE INSPECTION METHOD

(71) Applicants: Envision AESC Japan Ltd., Zama-shi, Kanagawa (JP); Automotive Energy Supply Corporation, Zama-Shi, Kanagawa (JP)

(72) Inventors: Koichi Kawamoto, Hiratsuka (JP); Shuji Yoshida, Tokyo (JP); Yutaka Suzuki, Kanagawa (JP); Takashi Matsuoka, Sagamihara (JP); Toshiharu Tanaka, Ebina (JP)

(73) Assignees: Automotive Energy Supply Corporation, Zama-Shi, Kanagawa (JP); Envision AESC Japan Ltd., Zama-shi, Kanagawa (JP)

( * ) Notice: Subject to any disclaimer, the term of this patent is extended or adjusted under 35 U.S.C. 154(b) by 76 days.

(21) Appl. No.: 14/760,907

(22) PCT Filed: Dec. 25, 2013

(86) PCT No.: PCT/JP2013/084677
§ 371 (c)(1),
(2) Date: Jul. 14, 2015

(87) PCT Pub. No.: WO2014/112307
PCT Pub. Date: Jul. 24, 2014

(65) Prior Publication Data
US 2015/0369779 A1 Dec. 24, 2015

(30) Foreign Application Priority Data
Jan. 15, 2013 (JP) .................................. 2013-004664

(51) Int. Cl.
*G01N 29/04* (2006.01)
*B23K 20/10* (2006.01)
*B23K 31/12* (2006.01)

(52) U.S. Cl.
CPC ............. *G01N 29/04* (2013.01); *B23K 20/10* (2013.01); *B23K 31/125* (2013.01); *G01N 2291/267* (2013.01); *H01L 2924/0002* (2013.01)

(58) Field of Classification Search
CPC .. G01N 29/04; G01N 2291/267; B23K 20/10; B23K 31/125
See application file for complete search history.

(56) References Cited

U.S. PATENT DOCUMENTS

| 5,500,492 A | * | 3/1996 | Kobayashi | ............ G06F 3/0433 178/18.04 |
| 2010/0015466 A1 | * | 1/2010 | Yoshioka | ............... B23K 20/10 428/615 |

(Continued)

FOREIGN PATENT DOCUMENTS

| CN | 1672856 A | 9/2005 |
| EP | 1516689 A1 | 3/2005 |

(Continued)

*Primary Examiner* — Ryan D Walsh
(74) *Attorney, Agent, or Firm* — Young Basile Hanlon & MacFarlane, P.C.

(57) ABSTRACT

A welding state inspection method for ultrasonic-welded plate-like members includes the steps of measuring energy that has been transmitted to an anvil when ultrasonic-welding a plurality of plate-like members stacked on the anvil while pressing a horn that vibrates against the plate-like members; and determining a quality of a welding state of the plate-like members on the basis of the energy measured in the measuring step.

4 Claims, 10 Drawing Sheets

(56) References Cited

U.S. PATENT DOCUMENTS

| | | | |
|---|---|---|---|
| 2010/0212429 A1* | 8/2010 | Isobe | G01N 29/069 73/602 |
| 2011/0155789 A1* | 6/2011 | Aoyagi | B23K 20/007 228/1.1 |
| 2014/0138012 A1* | 5/2014 | Spicer | B06B 3/00 156/64 |

FOREIGN PATENT DOCUMENTS

| | | | |
|---|---|---|---|
| JP | 05-115986 A | | 5/1993 |
| JP | H11197854 A | | 7/1999 |
| JP | 2000202644 A | | 7/2000 |
| JP | 2004351428 A | | 12/2004 |
| JP | 2005271028 A | * | 10/2005 |
| JP | 2008142739 A | * | 6/2008 |
| JP | 2010184252 A | | 8/2010 |
| JP | 2012035299 A | | 2/2012 |
| JP | 2012091213 A | | 5/2012 |

* cited by examiner

WELDING STATE INSPECTION METHOD

CROSS REFERENCE TO RELATED APPLICATION

The present application is based on Japanese Patent Application No. 2013-004664 filed on Jan. 15, 2013, the entire content of which is herein incorporated by reference.

TECHNICAL FIELD

The present invention relates to a welding state inspection method. In particular, the present invention relates to the welding state inspection method of inspecting a welding state of plate-like members that have been ultrasonic-welded together.

BACKGROUND

Ultrasonic welding performs solid-phase welding on two metal plates that have been placed on an anvil in a stacked state by pressing a horn that vibrates against the two metal plates.

In connection with this, in Japanese Patent Laid-Open Publication No. H5-115986, there is proposed an ultrasonic welding monitoring method of measuring a vibration of an anvil in ultrasonic-welding, comparing a measured waveform of vibration with a standard waveform, and determining the quality of ultrasonic welding. According to the monitoring method disclosed in Japanese Patent Laid-Open Publication No. H5-115986, the quality of the welding state of the two ultrasonic-welded metal plates can be determined with ease.

However, in the above-mentioned monitoring method, since the measured waveform of vibration is compared with the standard waveform, if the measured waveform is different from the standard waveform, a product will be determined to be a defective product. Therefore, there is such a problem that even a product that will be determined to be a non-defective product if a tension test is performed will be determined to be a defective product if the measured waveform is different from the standard waveform, and determination accuracy is low.

SUMMARY

The present invention has been made in order to solve the above-mentioned problem. Accordingly, an object of the present invention is to provide a welding state inspection method capable of accurately determining the quality of a welding state of plate-like members that have been ultrasonic-welded together.

The above-mentioned object of the present invention is attained by the following measures.

The welding state inspection method of the present invention has a measuring step and a determining step. The measuring step measures energy that has been transmitted to an anvil when ultrasonic-welding a plurality of plate-like members stacked on the anvil while pressing a horn that vibrates against the plate-like members. The determining step determines a quality of a welding state of the plate-like members on the basis of the energy measured in the measuring step.

According to the present invention, since the quality of the welding state of the plate-like members is determined on the basis of the energy that has been transmitted to the anvil, even when the measured waveform of vibration is different from the standard waveform, it can be correctly determined. That is, the quality of the welding state of the plate-like members can be accurately determined.

DESCRIPTION OF THE EMBODIMENTS

In the following, an embodiment of the present invention will be described with reference to the drawings. Incidentally in the drawings, the same numerals are assigned to the same members.

Figure 1:
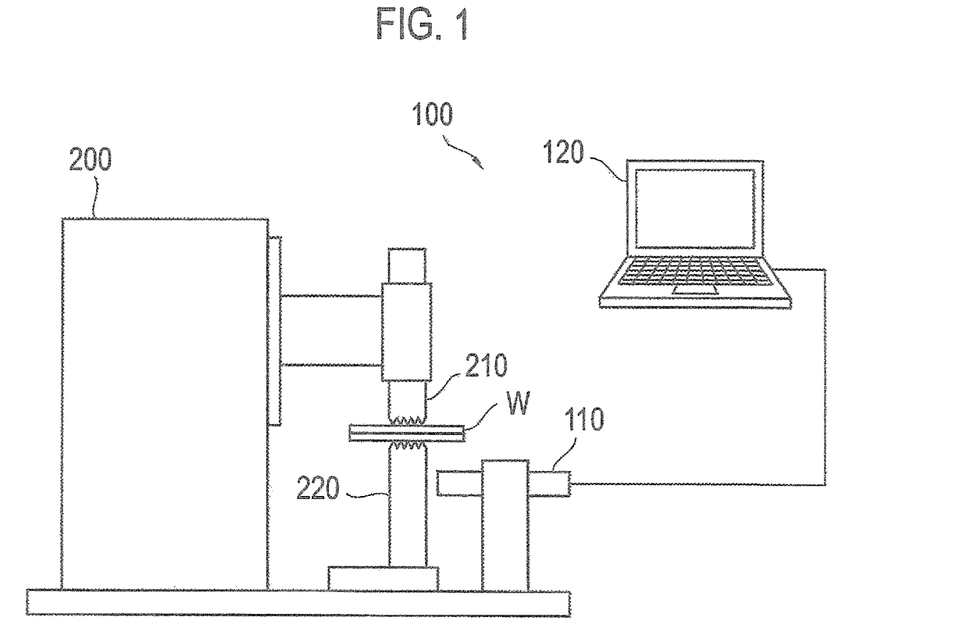
FIG. 1 is a diagram showing a schematic configuration of an inspection device to which a welding state inspection method according to one embodiment of the present invention is applied.

FIG. 1 is a diagram showing a schematic configuration of an inspection device 100 to which a welding state inspection method according to one embodiment of the present invention is applied.

The inspection device 100 inspects a welding state of plate materials W to be ultrasonic-welded by an ultrasonic welding device 200. The ultrasonic welding device 200 has a horn 210 that is pressed against the plate materials W to apply vibration thereto, and an anvil 220 on which the plate materials W are placed. Pluralities of projections each having a pyramid shape are respectively formed on leading ends of the horn 210 and the anvil 220 that are arranged so as to face each other on the ultrasonic welding device 200.

As shown in FIG. 1, the inspection device 100 includes a vibration sensor 110 that measures vibration amplitude of the anvil 220 of the ultrasonic welding device 200, and an analyzer 120 that determines the quality of the welding state of the plate materials W on the basis of a signal from the vibration sensor 110.

The vibration sensor 110 is arranged on a side face of the anvil 220, and measures the vibration amplitude of the anvil 220 in ultrasonic welding. The vibration sensor 110 is connected to the analyzer 120 via an A/D converter (not shown). As the vibration sensor 110, non-contact type displacement sensors such as an eddy current sensor, a laser Doppler displacement meter and so forth can be adopted.

The analyzer 120 determines the quality of the welding state of the plate materials W to be ultrasonic-welded together. The analyzer 120 analyzes vibration waveform data that the vibration sensor 110 can obtain by measuring the vibration amplitude of the anvil 220, and determines the quality of the welding state of the two plate materials W that have been ultrasonic-welded together. The analyzer 120 is, for example, a general personal computer.

Figure 2:
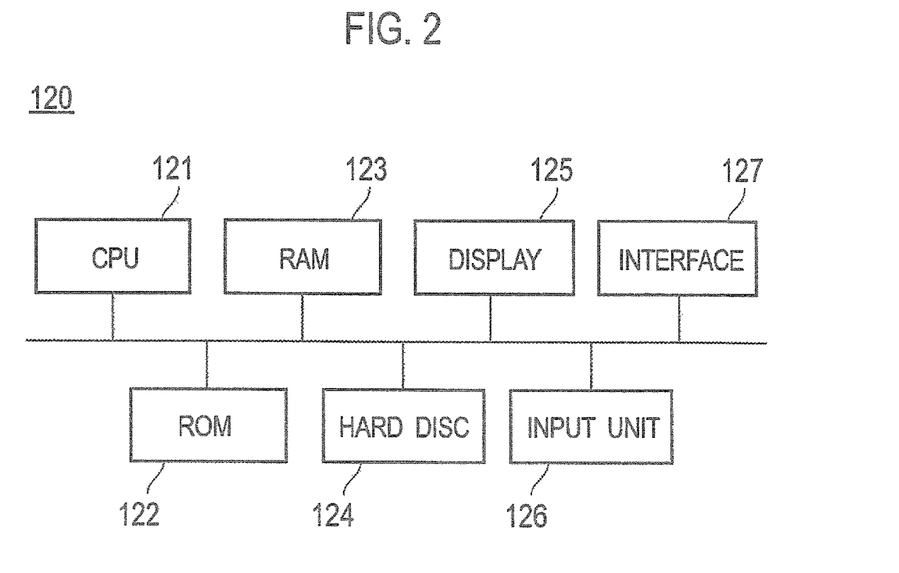
FIG. 2 is a block diagram showing a schematic configuration of an analyzer shown in FIG. 1.

FIG. 2 is a block diagram showing a schematic configuration of the analyzer 120. The analyzer 120 has a CPU 121, a ROM 122, a RAM 123, a hard disc 124, a display 125, an input unit 126, and an interface 127. These respective units are mutually connected via a bus.

The CPU 121 performs control of the above-mentioned respective units and various kinds of arithmetic processing according to a program. The ROM 122 stores in advance various kinds of programs and various kinds of data. The RAM 123 temporarily memorizes programs and data as a work area.

The hard disc 124 stores various kinds of programs and various kinds of data including an OS (Operating System). A data analysis program for analyzing the vibration waveform data obtained by measuring the vibration amplitude of the anvil 220 by the vibration sensor 110 is stored in the hard disc 124.

The display 125 is, for example, a liquid crystal display, and displays various kinds of information. The input unit 126 is, for example, a pointing device such as a keyboard, a touch panel and a mouse, and is used for inputting various kinds of information.

The interface 127 electrically connects together the analyzer 120 and the vibration sensor 110. The interface 127 receives a signal from the vibration sensor 110.

Incidentally, the analyzer 120 may include constitutional elements other than the above-mentioned constitutional elements, or may not include some of the above-mentioned constitutional elements.

The inspection device 100 configured as above determines the quality of the welding state of the plate materials W, on the basis of energy that has been transmitted to the anvil 220 when the plate materials W are ultrasonic-welded together by the ultrasonic welding device 200. In the following, with reference to FIG. 3 to FIG. 14, the welding state inspection method according to the present embodiment will be described in detail.

Figure 3:
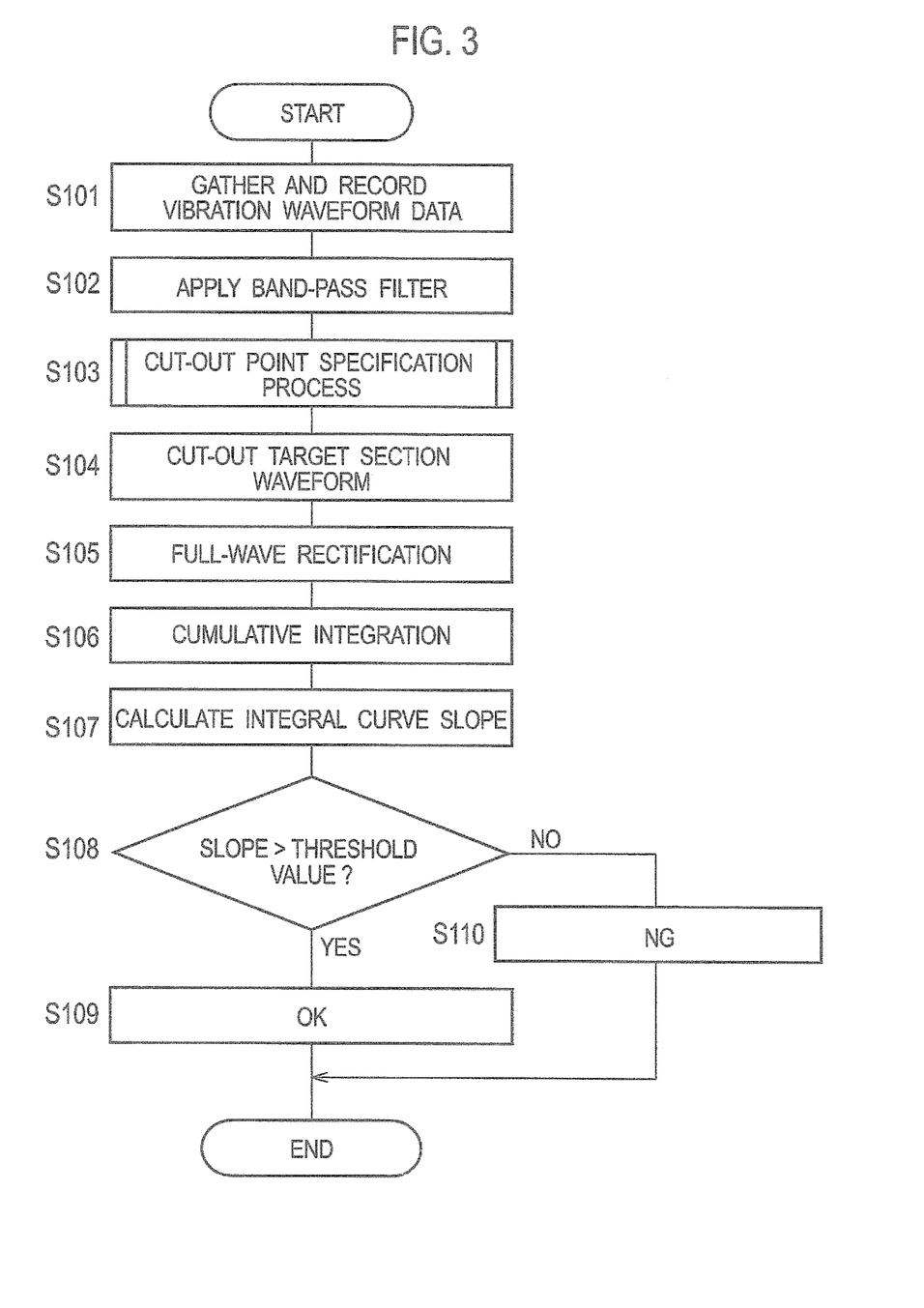
FIG. 3 is a flowchart showing a procedure of a data analysis process to be executed by the analyzer.

FIG. 3 is a flowchart showing the procedure of a data analysis process to be executed by the analyzer 120. Incidentally, an algorithm shown by the flowchart in FIG. 3 is memorized in the hard disc 124 of the analyzer 120 as a program, and is executed by the CPU 121.

First, the vibration waveform data are gathered and recorded (step S101). Specifically, while the ultrasonic welding device 200 performs ultrasonic welding on the plate materials W, the vibration amplitude of the anvil 220 is measured by the vibration sensor 110, and outputs from the vibration sensor 110 are gathered and recorded as the vibration waveform data.

Subsequently, a band-pass filter (hereinafter, referred to as a "BPF") is applied (step S102). Specifically, the BPF is applied to the vibration waveform data that have been gathered and recorded in the process shown in step S101, and data in a predetermined frequency band is extracted. The BPF is an FIR filter that, setting a vibration frequency (for example, 20 kHz) of the horn 210 as a center frequency, has a band width of ±500 Hz from the center frequency.

Figure 4:
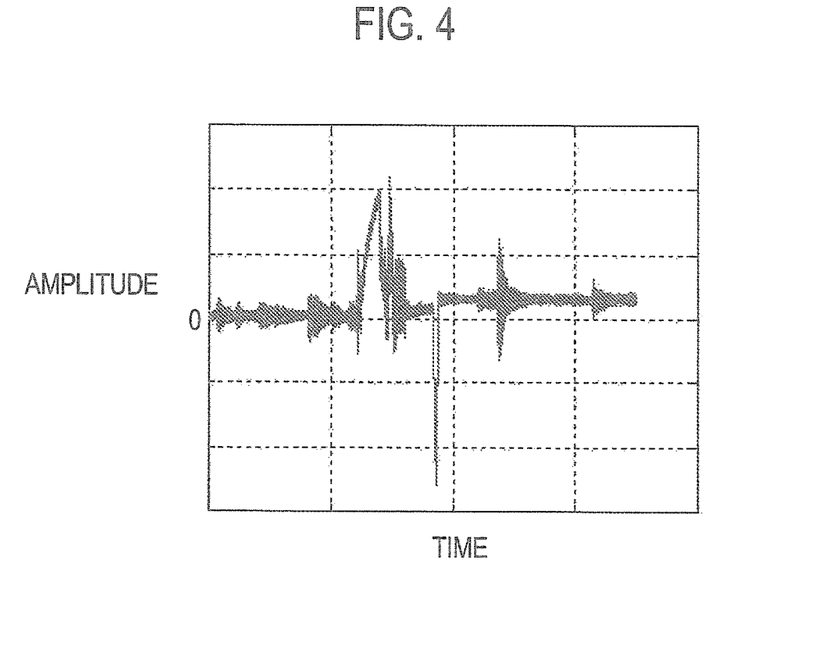
FIG. 4 is a diagram showing one example of vibration waveform data.
Figure 5:
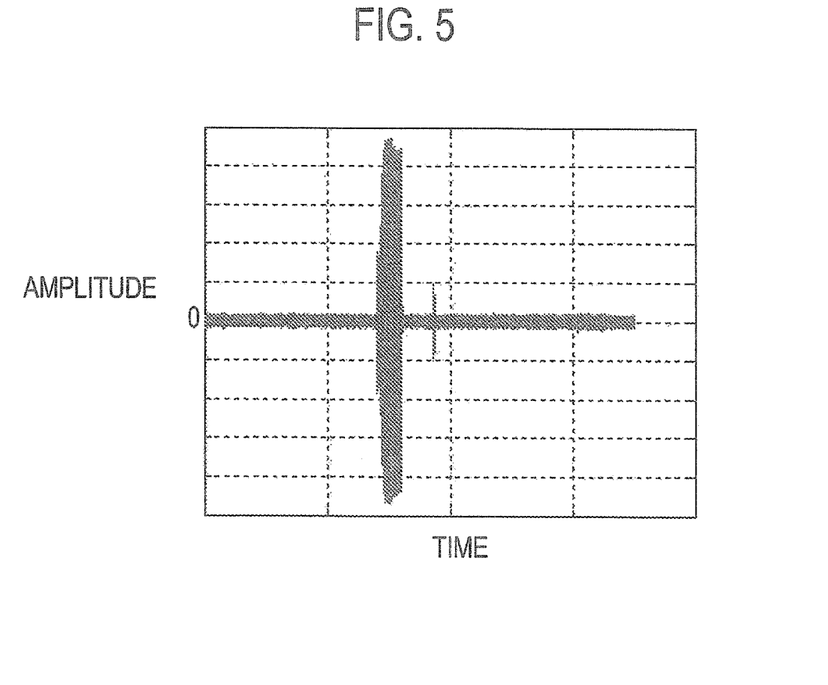
FIG. 5 is a diagram showing vibration waveform data to which a band-pass filter has been applied.

FIG. 4 is a diagram showing one example of the vibration waveform data, and FIG. 5 is a diagram showing the vibration waveform data to which the BPF has been applied. The vertical axis in FIG. 4 and FIG. 5 indicates the vibration amplitude (an output voltage of the vibration sensor 110) of the anvil 220, and the horizontal axis indicates a time (a sampling point number).

In the present embodiment, as shown in FIG. 4, the outputs from the vibration sensor 110 are gathered and recorded as the vibration waveform data. Data before the ultrasonic welding device 200 starts ultrasonic welding and after it has terminated ultrasonic welding are also included in the vibration waveform data. If the BPF is applied to the gathered and recorded vibration waveform data, vibration waveform data of, for example, the center frequency 20 kHz and the bandwidth ±500 Hz will be extracted from the vibration waveform data as shown in FIG. 5.

Subsequently, a cut-out point specification process is executed (step S103). Specifically, the cut-out point specification process of specifying a sampling point for cutting-out data on the time when the anvil 220 is vibrating from the vibration waveform data to which the BPF has been applied in the process shown in step S102 is executed.

Figure 6:
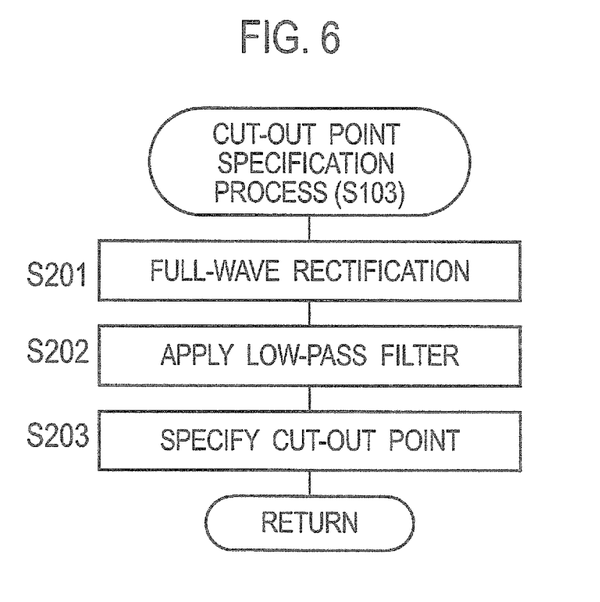
FIG. 6 is a flowchart showing a procedure of a cut-out point specification process shown in step S103 in FIG. 3.

FIG. 6 is a flowchart showing the procedure of the cut-out point specification process.

Figure 7:
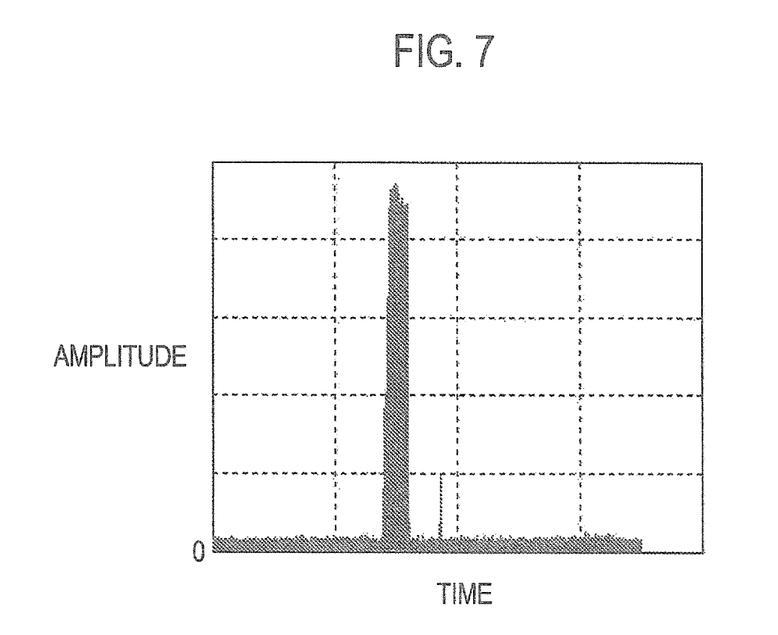
FIG. 7 is a diagram showing vibration waveform data in which full-wave rectification has been performed.

First, full-wave rectification (step S201) is performed. Specifically, full-wave rectification is performed on the vibration waveform data to which the BPF has been applied in the process shown in step S102. When full-wave rectification is performed, an amplitude value on the minus side of the vibration waveform data is inverted as shown in FIG. 7.

Figure 8:
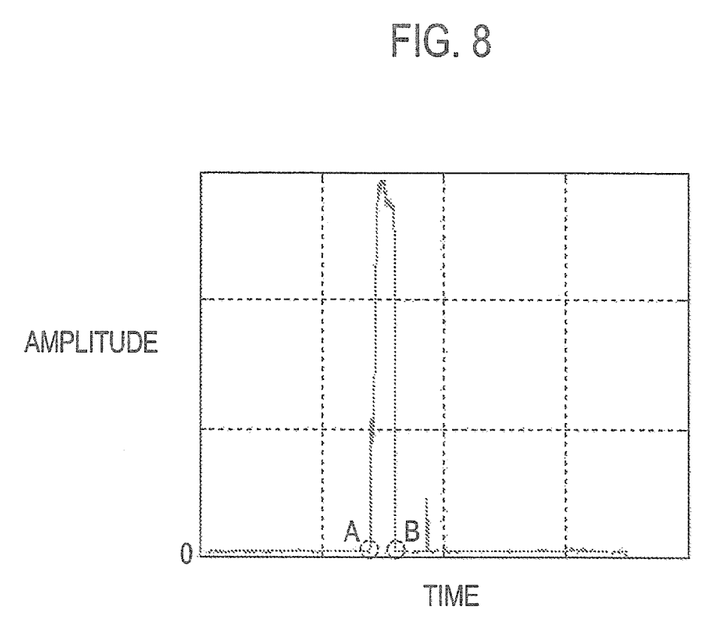
FIG. 8 is a diagram showing vibration waveform data to which a low-pass filter has been applied.

Subsequently, a low-pass filter (hereinafter, referred to as an "LPF") is applied (step S202). Specifically, the LPF is applied to the vibration waveform data in which full-wave rectification has been performed in the process shown in step S201. When the LPF is applied, an envelope of the vibration waveform data is extracted as shown in FIG. 8.

Then, a cut-out point is specified (step S203). Specifically, a start point and an end point for cutting-out data on the time when the anvil 220 is vibrating are specified from within the vibration waveform data, on the basis of the vibration waveform data to which the LPF has been applied in the process shown in step S202.

Figure 9:
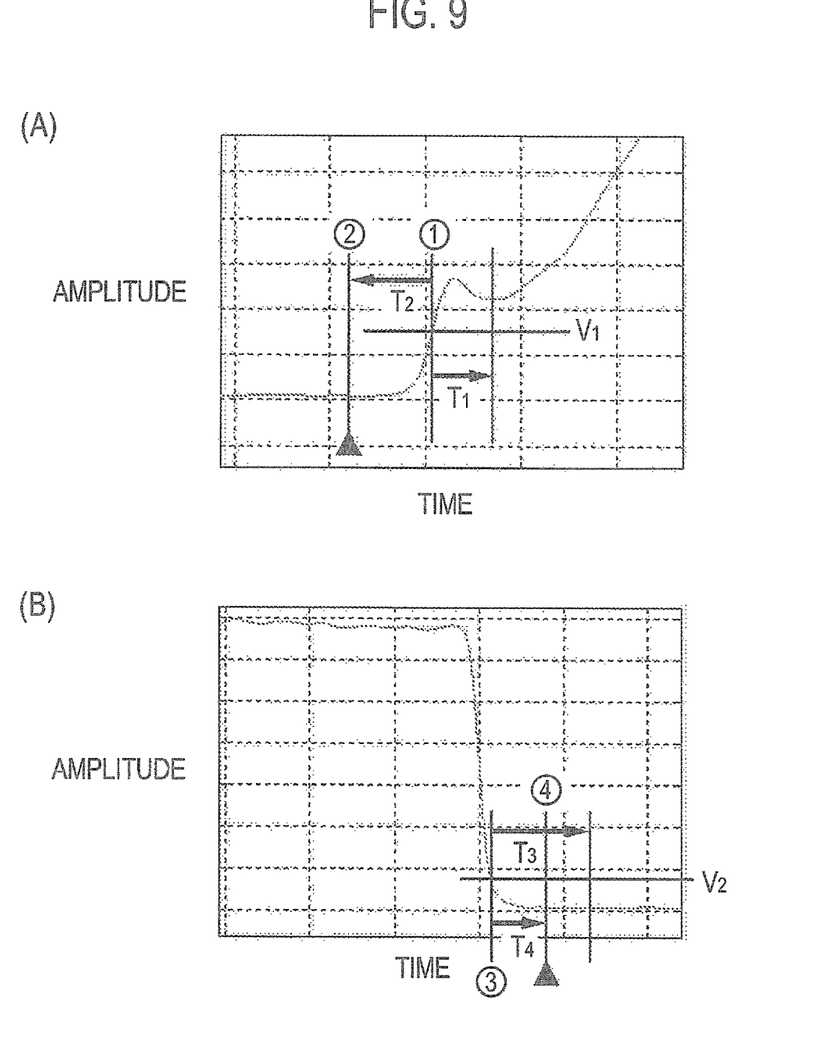
FIGS. 9(A) and 9(B) are diagrams for explaining the cut-out point specification process.

FIGS. 9(A) and 9(B) are diagrams for explaining the cut-out point specification process. FIG. 9(A) is an enlarged diagram of a part A surrounded by a broken line in FIG. 8, and FIG. 9(B) is an enlarged diagram of a part B surrounded by a broken line in FIG. 8.

In a case where the start point is to be specified, as shown in FIG. 9(A), first, a point of time (a sampling point 1) that the amplitude value of the vibration waveform data first exceeds a predetermined threshold value $V_1$ is recognized. Subsequently, it is checked that a state where the amplitude value exceeds the threshold value $V_1$ lasts for a predetermined time $T_1$ (a predetermined sampling point number). If it is confirmed that the state where the amplitude value exceeds the threshold value $V_1$ lasts for the predetermined time, a point of time (a sampling point 2) going back from the sampling point 1 for a predetermined time $T_2$ (a predetermined sampling point number) will be specified as the start point.

On the other hand, in a case where the end point is to be specified, as shown in FIG. 9(B), first, a point of time (a sampling point 3) that the amplitude value of the vibration waveform data first falls below a predetermined threshold value $V_2$ is recognized. Subsequently, it is checked that a state where the amplitude value falls below the threshold value $V_2$ lasts for a predetermined time $T_3$. If it is confirmed that the state where the amplitude value falls below the threshold value $V_2$ lasts for the predetermined time, a point of time (a sampling point 4) advancing from the sampling point 3 for a predetermined time $T_4$ will be specified as the end point.

As above, according to the cut-out point specification process shown in step S103 in FIG. 3, the sampling points for cutting-out the data on the time when the anvil 220 is vibrating are specified from the vibration waveform data.

Figure 10:
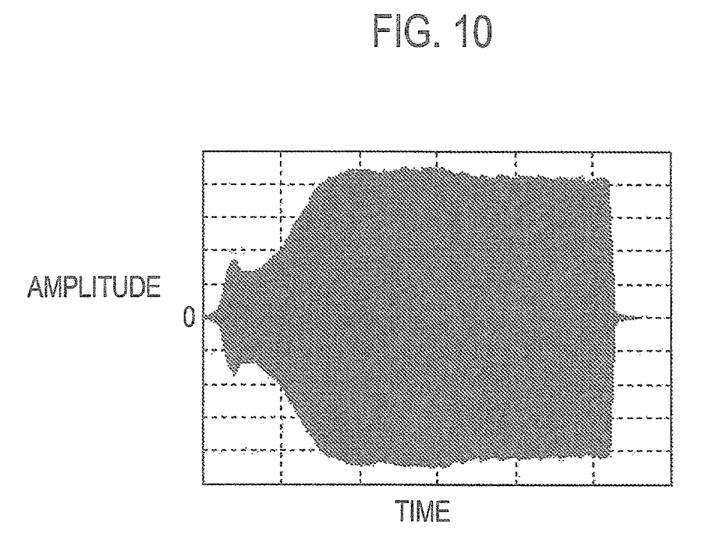
FIG. 10 is a diagram showing vibration waveform data in which a waveform of a target section has been cut-out.

Subsequently, a waveform of a target section is cut-out (step S104). Specifically, data on a time that is defined by the two cut-out points specified in the process shown in step S103 is cut-out from the vibration waveform data to which the BPF has been applied in the process shown in step S102. As a result, as shown in FIG. 10, vibration waveform data from which data unrelated to determination of the quality of the welding state has been removed is obtained.

Figure 11:
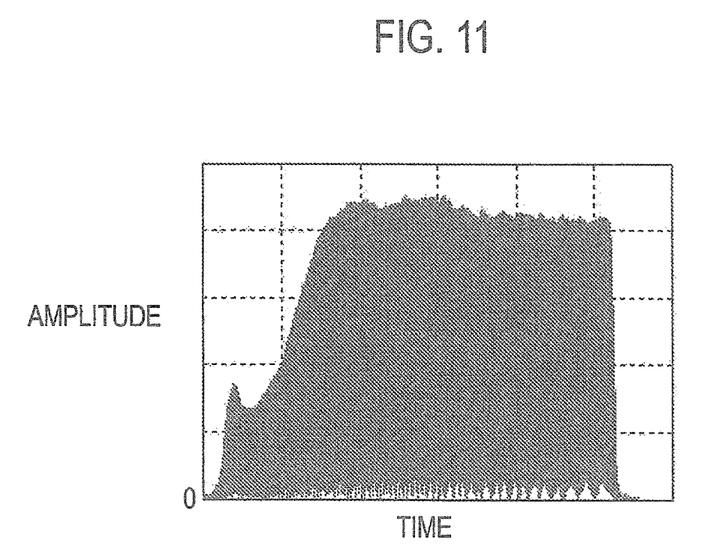
FIG. 11 is a diagram showing vibration waveform data in which full-wave rectification has been performed.

Subsequently, full-wave rectification is performed (step S105). Specifically, full-wave rectification is performed on the vibration waveform data that has been cut-out in the process shown in step S104. If full-wave rectification is performed, the amplitude value on the minus side of the vibration waveform data will be inverted as shown in FIG. 11.

Subsequently, cumulative integration is performed (step S106). Specifically, cumulative integration of the vibration waveform data in which full-wave rectification has been performed in the process shown in step S105 is performed. More specifically, the amplitude values of the respective sampling points of the vibration waveform data are accumulated.

Subsequently, a slope of an integral curve is calculated (step S107). Specifically, the slope of the integral curve of the vibration waveform data is calculated by dividing a cumulative integration value of the vibration waveform data in which cumulative integration has been performed in the process shown in step S106 by a time (an integral time) from the start point to the end point of the integral curve.

Figure 12:
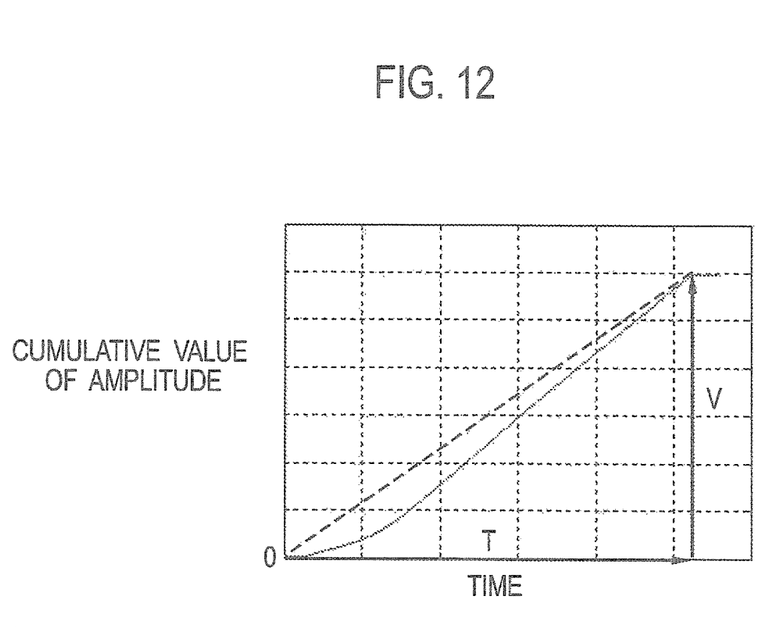
FIG. 12 is a diagram showing a result of cumulative integration of the vibration waveform data.

FIG. 12 is a diagram showing a result of cumulative integration of the vibration waveform data. In the present embodiment, a slope (V/T) of the integral curve of the vibration waveform data is calculated by dividing a cumulative integration value V of the vibration waveform data by a time T from the start point to the end point of the integral curve. Incidentally, the cumulative integration value V corresponds to an area value of the vibration waveform data shown in FIG. 11. In addition, the cumulative integration value V and the area value of the vibration waveform data correspond to energy that has been transmitted to the anvil 220 when the plate materials W are ultrasonic-welded together by the ultrasonic welding device 200.

Subsequently, whether or not the slope of the integral curve exceeds a predetermined threshold value is judged (step S108). Specifically, whether or not the slope of the integral curve that has been calculated in the process shown in step S107 exceeds the predetermined threshold value is judged. Here, the predetermined threshold value is a value that has been statistically obtained by taking data on the slopes of the integral curves in regard to a plurality of sets of the plate materials that are favorable in welding state.

In a case where it is judged that the slope of the integral curve exceeds the predetermined threshold value (step S108: YES), it is judged that the welding state is favorable (step S109) and the process is terminated. For example, that the welding state is favorable is displayed on the display 125 of the analyzer 120, and the process is terminated.

On the other hand, in a case where it is judged that the slope of the integral curve does not exceed the predetermined threshold value (step S108: NO), it is judged that the welding state is not favorable (step S110), and the process is terminated. For example, that the welding state is unfavorable is displayed on the display 125 of the analyzer 120, and the process is terminated.

As above, according to the process of the flowchart shown in FIG. 3, first, the vibration amplitude of the anvil 220 is measured by the vibration sensor 110, and the vibration waveform data are gathered and recorded. Subsequently, the vibration waveform data are integrated, and the cumulative integration value is calculated. Then, the quality of the welding state of the plate materials W is determined on the basis of the cumulative integration value of the vibration waveform data.

That is, according to the welding state inspection method of the present embodiment, the energy that has been transmitted to the anvil 220 when the plate materials W are ultrasonic-welded together by the ultrasonic welding device 200 is measured, and the quality of the welding state of the plate materials W is determined on the basis of the measured energy. According to such a configuration, the quality of the welding state of the ultrasonic-welded plate materials W can be accurately determined.

In the following, the operational effects of the welding state inspection method according to the present embodiment will be described in detail with reference to FIG. 13 and FIG. 14.

Figure 13:
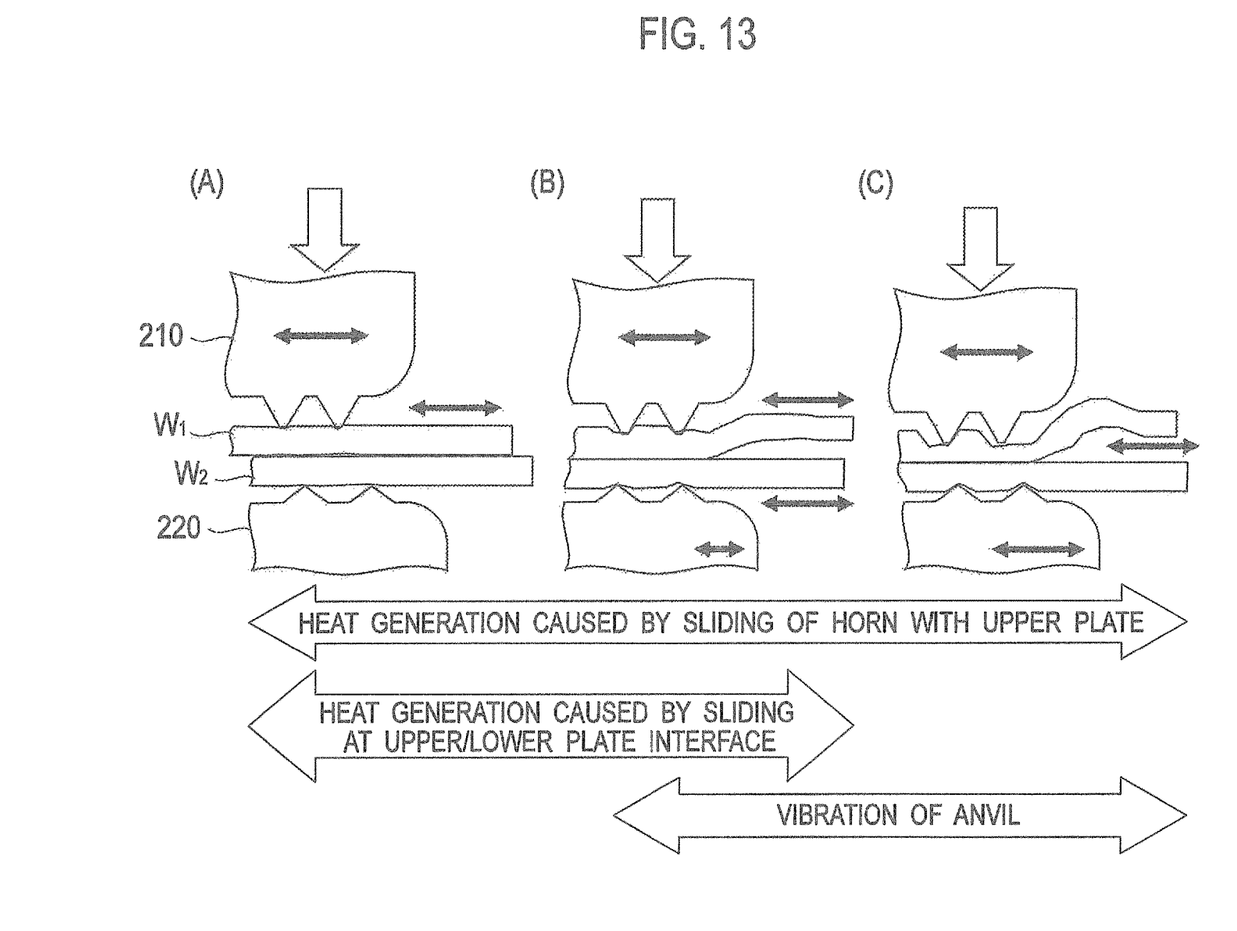
FIG. 13 is a diagram showing the behavior of an anvil in ultrasonic welding.

FIG. 13 is a diagram showing the behavior of the anvil 220 in ultrasonic welding.

As shown in FIG. 13(A), directly after start of ultrasonic welding, the two plate materials $W_1$, $W_2$ are not yet welded together, and the vibration of the horn 210 is transmitted to only the upper side plate material $W_1$ in the two plate materials $W_1$, $W_2$. Therefore, the anvil 220 does not vibrate, and heat generation caused by sliding of the horn 210 with the plate material $W_1$ and heat generation caused by sliding of the plate material $W_1$ with the plate material $W_2$ occur.

As shown in FIG. 13(B), when the plate material $W_1$ and the plate material $W_2$ begin to be welded together, the vibration of the horn 210 is transmitted to the anvil 220, and the anvil 220 begins to vibrate.

Then, as shown in FIG. 13(C), when welding of the plate material $W_1$ with the plate material $W_2$ is advanced, the plate material $W_1$ and the plate material $W_2$ no longer slide and heat generation caused by sliding of the plate material $W_1$ with the plate material $W_2$ ceases. On the other hand, the vibration of the anvil 220 is increased. Incidentally, the ultrasonic welding device 200 applies power to the horn 210 so as to maintain the amplitude and an applied pressure of the horn 210 constant.

As above, in ultrasonic welding, the energy that is transmitted from the horn 210 to the anvil 220 via the plate materials $W_1$, $W_2$ is changed in accordance with the welding state at a welded interface of the two plate materials $W_1$, $W_2$. In addition to this, also owing to influence of deformation, stains and so forth of the plate materials $W_1$, $W_2$, even if the vibration amplitude of the horn 210 is measured, a correlation with the welding state at the welded interface of the plate materials $W_1$, $W_2$ cannot be obtained, and the welding state cannot be correctly grasped.

On the other hand, in the welding state inspection method of the present embodiment, the energy that has been transmitted to the anvil 220 that is a real requirement of ultrasonic welding is measured by measuring the vibration amplitude of the anvil 220. Therefore, a result of measurement that has correctly reflected the welding state of the plate materials W1, W2 that changes with the lapse of time is obtained, and it becomes possible to accurately determine the quality of the welding state.

In addition, in the welding state inspection method of the present embodiment, the vibration amplitude of the anvil 220 is measured by the non-contact type vibration sensor 110. Accordingly, the own weight of the sensor does not influence a vibrational state as by a contact type vibration sensor, and the behavior of the anvil 220 can be correctly measured.

Figure 14:
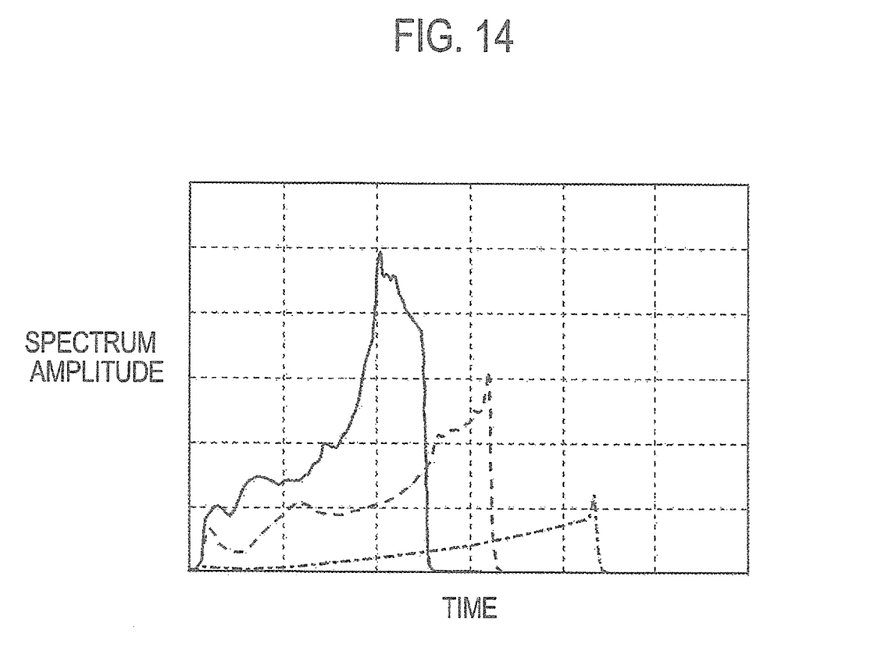
FIG. 14 is a diagram for explaining advantageous effects of the welding state inspection method.

FIG. 14 is a diagram for explaining the advantageous effects of the welding state inspection method according to the present embodiment. In FIG. 14, vibration waveforms indicated by a solid line and a broken line are vibration waveforms of non-defective products that are judged to be favorable in welding state (welding strength) by a tension test. On the other hand, a vibration waveform indicated by a one-point chain line in FIG. 14 is a waveform of a defective product that is judged to be unfavorable in welding state by the tension test.

As shown in FIG. 14, the defective product is small in energy that has been transmitted to the anvil in comparison with the non-defective products. On the other hand, when the vibration waveform of the non-defective product indicated by the solid line is compared with the vibration waveform of the non-defective product indicated by the broken line, the waveforms are different from each other. In the conventional monitoring method of comparing the measured waveform with the standard waveform, the product of the vibration waveform indicated by the broken line is determined to be the defective product.

However, since the welding state inspection method of the present embodiment determines the quality of the welding state on the basis of the energy that has been transmitted to the anvil, even the product that is determined to be the defective product when focusing on the measured waveform can be determined to be the non-defective product.

Like this, according to the welding state inspection method of the present embodiment, determination accuracy of the welding state of the plate materials is improved. As a result, the products determined to be the defective products are reduced and the yield of the products is improved.

As above, the present embodiment so described has the following advantageous effects.

(a) The welding state inspection method of the present embodiment determines the quality of the welding state of the plate materials on the basis of the energy that has been transmitted to the anvil. Accordingly, even when the measured waveform of the vibration amplitude of the anvil is different from the standard waveform, correct determination can be performed. That is, the quality of the welding state of the plate materials can be accurately determined.

(b) The welding state inspection method of the present embodiment integrates the vibration waveform data obtained by measuring the vibration amplitude of the anvil by the vibration sensor, and determines the quality of the welding state of the plate materials on the basis of the result of integration of the vibration waveform data. Accordingly, the quality of the welding state can be determined with ease by quantifying the energy that has been transmitted to the anvil.

(c) The welding state inspection method of the present embodiment determines that when the value obtained by dividing the integration value of the vibration waveform data by the integration time is larger than the predetermined threshold value, the welding state of the plate materials is favorable. Accordingly, a variation in welding time is absorbed and the stability of determination is improved.

(d) The welding state inspection method of the present embodiment cut-outs the data on the time when the anvil is vibrating from within the vibration waveform data and integrates the cut-out data. Accordingly, the data amount is reduced and the quality of the welding state can be determined in a short time.

(e) The welding state inspection method of the present embodiment extracts the data from the vibration waveform data by applying the BPF of the frequency band that is defined by the vibration frequency of the horn. Accordingly, disturbance (noise) contained in the vibration waveform data can be removed.

(f) The center frequency of the BPF matches the vibration frequency of the horn. Accordingly, only the energy that has been transmitted from the horn can be selectively extracted.

As above, the welding state inspection method of the present invention has been described in one embodiment that has been described. However, it goes without saying that a person skilled in the art can appropriately perform addition, modification and omission on the present invention within a range of its technical idea.

For example, in the above-mentioned embodiment, the quality of the welding state of the plate materials has been determined on the basis of the slope of the integral curve of the vibration waveform data. However, the method of determining the quality of the welding state on the basis of the energy that has been transmitted to the anvil is not limited to the method utilizing the slope of the integral curve. For example, in a case where the cumulative integration value of the vibration waveform data (the area value of the vibration waveform data) reaches a predetermined value, it may be determined that the welding state of the plate materials is favorable.

The invention claimed is:

1. A welding state inspection device comprising a vibration sensor and a computer comprising a processor, a memory in electronic communication with the processor, and instructions stored in the memory, the instructions being executable to implement a welding state inspection method comprising:
   measuring energy that has been transmitted to an anvil when ultrasonic-welding a plurality of plate members stacked on the anvil while pressing a horn that vibrates against the plate members by
      measuring, by the vibration sensor, vibration amplitude of the anvil; and
      calculating, by the processor, time integration of vibration data, wherein the vibration data is obtained by measuring the vibration amplitude of the anvil;
   determining, by the processor, a welding state of the plate members on the basis of a result of time integration in the calculating operation, wherein the vibration sensor is a non-contact type displacement sensor
   comparing, by the processor, a value obtained by dividing an integration value of the vibration data by an integration time with a threshold value that has been set in advance; and
   determining, by the processor, that the welding state of the plate members is favorable in a case where the value obtained by dividing the integration value by the integration time is larger than the threshold value.

2. A welding state inspection device comprising a vibration sensor and a computer comprising a processor, a memory in electronic communication with the processor, and instructions stored in the memory, the instructions being executable to implement a welding state inspection method comprising:

measuring energy that has been transmitted to an anvil when ultrasonic-welding a plurality of plate members stacked on the anvil while pressing a horn that vibrates against the plate members by         measuring, by the vibration sensor, vibration amplitude of the anvil; and         calculating, by the processor, time integration of vibration data, wherein the vibration data is obtained by measuring the vibration amplitude of the anvil; and     determining, by the processor, a welding state of the plate members on the basis of a result of time integration in the calculating operation, wherein the vibration sensor is a non-contact type displacement sensor wherein the measuring operation is prior to the calculating operation, and the measuring operation further includes:

extracting, by the processor, data of a period of time from the vibration data, the period of time being when the anvil is vibrating; and     integrating, by the processor, the extracted data of the period of time.

3. A welding state inspection device comprising a vibration sensor and a computer comprising a processor, a memory in electronic communication with the processor, and instructions stored in the memory, the instructions being executable to implement a welding state inspection method comprising:

measuring energy that has been transmitted to an anvil when ultrasonic-welding a plurality of plate members stacked on the anvil while pressing a horn that vibrates against the plate members by         measuring, by the vibration sensor, vibration amplitude of the anvil; and         calculating, by the processor, time integration of vibration data, wherein the vibration data is obtained by measuring the vibration amplitude of the anvil; and     determining, by the processor, a welding state of the plate members on the basis of a result of time integration in the calculating operation, wherein the vibration sensor is a non-contact type displacement sensor, wherein the measuring operation is prior to the calculating operation, and the measuring operation further includes:

applying, by the processor, a band-pass filter of a frequency band defined by a vibration frequency of the horn to extract data of the frequency band from the vibration data; and     integrating, by the processor, the extracted data of the frequency band.

4. The welding state inspection device according to claim 3, wherein a center frequency of the band-pass filter matches the vibration frequency of the horn.

\* \* \* \* \*